United States Patent
Nagano et al.

(10) Patent No.: US 7,399,318 B2
(45) Date of Patent: Jul. 15, 2008

(54) STABLE COMPOSITION FOR HAIR DYE

(75) Inventors: Junko Nagano, Kanagawa (JP); Kazuki Sugiyama, Kanagawa (JP); Yasuko Matsumura, Kanagawa (JP); Kunihide Hoshino, Kanagawa (JP); Takashi Aida, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 224 days.

(21) Appl. No.: 11/384,306

(22) Filed: Mar. 21, 2006

(65) Prior Publication Data

US 2006/0218730 A1    Oct. 5, 2006

(30) Foreign Application Priority Data

Apr. 4, 2005 (JP) ............ P.2005-107223

(51) Int. Cl.
*A61Q 5/10* (2006.01)

(52) U.S. Cl. .............. 8/405; 8/561; 8/582; 8/587; 8/607; 8/609

(58) Field of Classification Search .......... 8/405, 8/561, 582, 587, 607, 609
See application file for complete search history.

(56) References Cited

U.S. PATENT DOCUMENTS

| | | | |
|---|---|---|---|
| 2002/0058017 A1 | 5/2002 | Tajima et al. | 424/70.1 |
| 2003/0180238 A1* | 9/2003 | Sakurai et al. | 424/62 |

FOREIGN PATENT DOCUMENTS

| | | |
|---|---|---|
| EP | 0 347 596 | 12/1989 |
| EP | 1 190 696 | 3/2002 |
| EP | 1 346 720 | 9/2003 |
| JP | 7-82121 | 3/1995 |
| JP | 7-309732 | 11/1995 |
| JP | 9-136818 | 5/1997 |
| JP | 9-315948 | 12/1997 |
| JP | 2000-344629 | 12/2000 |
| JP | 2003-344638 | 12/2000 |
| JP | 2002-97122 | 4/2002 |
| JP | 2003-137758 | 5/2003 |
| JP | 2003-277246 | 10/2003 |
| JP | 2003-321697 | 11/2003 |
| JP | 2004-107208 | 4/2004 |

OTHER PUBLICATIONS

Yamamoto, et al., "Olfactory study on optically active citronellyl derivatives", *Flavour and Fragrance Journal*, vol. 19 (2004), pp. 121-133.

* cited by examiner

*Primary Examiner*—Eisa B Elhilo
(74) *Attorney, Agent, or Firm*—Fitzpatrick, Cella, Harper & Scinto

(57) ABSTRACT

The present invention relates to a stable composition for hair dye, which comprises at least one compound selected from dihydrocitronellyl nitrile, 2,2,6-trimethylcyclohexane carboxylic acid ethyl ester, 2-ethyl-4-(2,2,3-trimethyl-3-cyclopenten-1-yl)-2-buten-1-ol, 2,2,6-trimethylcyclohexyl-3-hexanol, 1-(2-methyl-2-propenyloxy)-2,2,4-trimethylpentan-3-ol, thioglycerin, dibutyl sulfide, thiogeraniol, thiocineol, 2-methyl-4-propyl-1,3-oxathian, 4-methoxy-2-methyl-2-butanethiol and the like. The stable composition for hair dye has a superior effect in masking a malodor originated from components such as ammonia formulated in hair dye composition such as composition for hair dye, and is also stable in an alkaline product and an acidic solution product.

8 Claims, No Drawings

STABLE COMPOSITION FOR HAIR DYE

FIELD OF THE INVENTION

The present invention relates to a stable composition for hair dye, which has a superior effect to mask malodors originated from substances such as ammonia, is stable in alkaline and acidic solutions for a long period of time and is also stable without changing color tones for a long period of time. It further relates to a hair dye composition containing the stable composition for hair dye.

BACKGROUND OF THE INVENTION

A lot of hair dyes are constituted from two types of preparations called a first preparation (to be referred sometimes to as "hair dye first preparation" hereinafter) and a second preparation (to be referred sometimes to as "hair dye second preparation" hereinafter). The first preparation contains dye intermediates including, e.g., an alkaline agent such as ammonia or an alkanolamine and a surfactant, and the second preparation contains, e.g., an oxidizing agent such as hydrogen peroxide and a pH adjusting agent. The main role of the first preparation is to effect penetration of the dye intermediates and oxidizing agent into hair through swelling of hair by the alkaline agent, and the main role of the second preparation is to remove melanin pigment from hair, develop a color through mutual binding of molecules of the dye intermediates and thereby fix the pigment into hair.

Various types of deodorant compositions for hair dyes have been examined in order to mask malodors originated from the malodors such as of ammonia or the alkanolamine formulated in the first preparation. However, since the first preparation generally shows an alkalinity of from pH 8 to 11 due to large amount of the formulated ammonia, it is required that a fragrance to be formulated has a property of being stable to the alkaline nature.

To date, stability and masking effect of various types of fragrance components have been examined, and deodorant compositions containing specified fragrance have been reported. For example, a method for masking an ammoniacal malodor or a solvent malodor of an aromatic alcohol by using a hair dye treatment composition containing cis-3-hexenol as a fragrance is disclosed (Patent Document 1). Further, methods in which specified fragrances are used are also disclosed (Patent Documents 2 to 6). These methods in which the above-described fragrances such as cis-3-hexenol are merely used can improve the malodor at the time of filling a hair dye product in a container. However, these methods have problems in that, after such filling, the masking effect becomes weak and cannot be exerted for a long period of time due to the change of the odor quality, and further, after the treatment, the masking effect becomes weak due to the weakness of the retention property of odor. Therefore, these methods cannot be regarded to be fully satisfied.

On the other hand, a dye component in hair dye base materials is high in reactivity, and therefore, there has been an inconvenience that, even at a stage in which the hair dye is stored before it is applied to hair, a polymerization occurs in the presence of oxygen in the air and thereby color is developed. Accordingly, various types of improvements for solving the above inconvenience have so far been made.

As one method, there may be mentioned a method in which the hair dye is blocked from air. Namely, an improvement has been made such that the hair dye is produced or allowed to be a commercial product in an atmosphere in which the hair dye is hardly in contact with oxygen by removing oxygen dissolved in a base material or by purging a container to which the base materials are stored with an inert gas which does not cause a reaction or the like. For example, in Patent Document 7, it is described that a mixing operation of components constituting a hair dye composition is conducted in an atmosphere in which an oxygen concentration is 0.00015% or less. However, in order to perform such an operation as described above, there is a problem in that economical burden is large. Furthermore, since highly-reactive dye compounds are apt to be degenerated and hair dying effect comes to be deteriorated along a passage of time, it is necessary to pay a great effort for keeping a value as a commercial product.

As another method, there may be mentioned a method of using a medicament. Namely, there is a method in which a given type of reducing agent, for example, a sulfite, vitamin C (ascorbic acid and salts thereof) or the like is added to the base materials and an active species generated in the base materials is trapped for preventing a deterioration of a hair dyeing effect over time by preventing a degeneration or the like of a highly-reactive dye compound (for example, Patent Documents 8 and 9). Although the above method is effective to a given extent, when an amount of the medicament to be used is large, for example, when it is more than 1% by weight, the dye is subjected to a reducing action to cause a problem in color development or an irritation to the skin, which is not preferred (for example, Patent Document 10). Moreover, since some of medicaments to be used have high penetrability into hair and are likely to cut a keratin protein through the reduction reaction, there is a fear that decrease of hair strength arises (Patent Document 11).

Still further, a method in which stabilization is realized by suppressing bonding or reaction between dye molecules by the addition of a surfactant is disclosed (for example, Patent Document 10). However, the effect of stability is not sufficient.

Patent Documents cited herein are as follows.
Patent Document 1: JP-A-2002-97122
Patent Document 2: JP-A-2000-344629
Patent Document 3: JP-A-2003-137758
Patent Document 4: JP-A-2003-277246
Patent Document 5: JP-A-2003-321697
Patent Document 6: JP-A-2004-107208
Patent Document 7: JP-A-2000-344638
Patent Document 8: JP-A-9-136818
Patent Document 9: JP-A-7-309732
Patent Document 10: JP-A-7-82121
Patent Document 11: JP-A-9-315948

SUMMARY OF THE INVENTION

The-present invention contemplates providing a stable composition for hair dye which can be used in the hair dye or a hair dye first preparation. That is, it is to provide a stable composition for hair dye, in which the used components show excellent effect to mask ammoniacal stimulating malodors when formulated in the hair dye first preparation and show excellent effect to mask the base material malodors, which renders possible masking of various types of malodors generated during bleaching of hair and hair dye treatment starting from the generation of oxygen due to decomposition of hydrogen peroxide after mixing with a hair dye second preparation and also retaining of desirable odor after the treatment, and which also gives no negative effect on the dyeing ability of the hair dye. Further provided is a stable composition for hair dye, which has excellent effect in masking malodors during a period of from before the hair dye treatment to after the treatment.

In other words, an object of the present invention is to find a stable composition for hair dye which is stable in an alkaline aqueous solution having a pH value of from 8 to 11 and a hydrogen peroxide-containing acidic solution having a pH value of from 2 to 4, without causing changes in odor and color for a prolonged period of time, and has remarkably excellent effect in masking an ammoniacal malodor.

With the aim of solving above problems, the present inventors have conducted intensive studies and found, as a result, that a specified fragrance is stable in alkaline and acidic solutions, has an excellent masking effect, retains a desirable odor for a while after the hair dye treatment and does not give a negative effect on dyeing ability of the hair dye, and have reached the present invention by further continuing the studies.

Accordingly, the invention relates to the followings.

(1) A method for stabilizing at least one of odor and color of a hair dye composition, which comprises incorporating into the hair dye composition at least one compound selected from dihydrocitronellyl nitrile, 2,2,6-trimethylcyclohexane carboxylic acid ethyl ester, 2-ethyl-4-(2,2,3-trimethyl-3-cyclopenten-1-yl)-2-buten-1-ol, 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, 2-methyl-4-(2,2,3-trimethyl-3-cyclopenten-1-yl)-2-buten-1-ol, tri(cis-3-hexenyl) orthoformate, thioglycerin, dibutyl sulfide, thiogeraniol, thiocineol, limonenethiol, 2-methyl-4-propyl-1,3-oxathian, 4-methoxy-2-methyl-2-butanethiol, 4-ethoxy-2-methyl-2-butanethiol, and 5-methoxy-3-methyl-3-pentanethiol.

(2) A method for stabilizing at least one of odor and color of a hair dye composition, which comprises incorporating into the hair dye composition at least one compound selected from dihydrocitronellyl nitrile, 2,2,6-trimethylcyclohexane carboxylic acid ethyl ester, 2-ethyl-4-(2,2,3-trimethyl-3-cyclopenten-1-yl)-2-buten-1-ol, 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, 2-methyl-4-(2,2,3-trimethyl-3-cyclopenten-1-yl)-2-buten-1-ol, and tri(cis-3-hexenyl) orthoformate as component A; and at least one compound selected from thioglycerin, dibutyl sulfide, thiogeraniol, thiocineol, limonenethiol, 2-methyl-4-propyl-1,3-oxathian, 4-methoxy-2-methyl-2-butanethiol, 4-ethoxy-2-methyl-2-butanethiol, and 5-methoxy-3-methyl-3-pentanethiol as component B.

(3) The method according to (1) above, which further comprises incorporating into the hair dye composition at least one compound selected from isobutyl quinoline, 2,6-nonadienol, 2-methyl-3-methoxypyrazine, amyl cyclopentanone, dihydropentamethyl indanone, 9-decen-1-ol, dihydroanethole, dihydromyrcenol, cis-3-hexenyl acetate, acetyl diisoamylene, 2,6-dimethyl-5-heptenal, acetaldehyde ethyl cis-3-hexenyl acetal, geranyl nitrile, citronellyl nitrile, citronellyl acetate, ethyl benzoate, phenyl ethyl acetate, 3,7-dimethyl-7-methoxyoctan-2-ol, phenyl propyl alcohol, 1-methyl-4-(4-methylpentyl)-3-cyclohexene carbaldehyde, coumarin, 3-pentyl tetrahydropyranyl acetate, and nopyl acetate as component C.

(4) The method according to (2) above, which further comprises incorporating into the hair dye composition at least one compound selected from isobutyl quinoline, 2,6-nonadienol, 2-methyl-3-methoxypyrazine, amyl cyclopentanone, dihydropentamethyl indanone, 9-decen-1-ol, dihydroanethole, dihydromyrcenol, cis-3-hexenyl acetate, acetyl diisoamylene, 2,6-dimethyl-5-heptenal, acetaldehyde ethyl cis-3-hexenyl acetal, geranyl nitrile, citronellyl nitrile, citronellyl acetate, ethyl benzoate, phenyl ethyl acetate, 3,7-dimethyl-7-methoxyoctan-2-ol, phenyl propyl alcohol, 1-methyl-4-(4-methylpentyl)-3-cyclohexene carbaldehyde, coumarin, 3-pentyl tetrahydropyranyl acetate, and nopyl acetate as component C.

(5) A hair dye composition, which comprises a stable composition for hair dye comprising at least one compound selected from dihydrocitronellyl nitrile, 2,2,6-trimethylcyclohexane carboxylic acid ethyl ester, 2-ethyl-4-(2,2,3-trimethyl-3-cyclopenten-1-yl)-2-buten-1-ol, 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, 2-methyl-4-(2,2,3-trimethyl-3-cyclopenten-1-yl)-2-buten-1-ol, tri(cis-3-hexenyl) orthoformate, thioglycerin, dibutyl sulfide, thiogeraniol, thiocineol, limonenethiol, 2-methyl-4-propyl-1,3-oxathian, 4-methoxy-2-methyl-2-butanethiol, 4-ethoxy-2-methyl-2-butanethiol, and 5-methoxy-3-methyl-3-pentanethiol.

(6) A hair dye composition, which comprises a stable composition for hair dye comprising at least one compound selected from dihydrocitronellyl nitrile, 2,2,6-trimethylcyclohexane carboxylic acid ethyl ester, 2-ethyl-4-(2,2,3-trimethyl-3-cyclopenten-1-yl)-2-buten-1-ol, 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, 2-methyl-4-(2,2,3-trimethyl-3-cyclopenten-1-yl)-2-buten-1-ol, and tri(cis-3-hexenyl) orthoformate as component A; and at least one compound selected from thioglycerin, dibutyl sulfide, thiogeraniol, thiocineol, limonenethiol, 2-methyl-4-propyl-1,3-oxathian, 4-methoxy-2-methyl-2-butanethiol, 4-ethoxy-2-methyl-2-butanethiol, and 5-methoxy-3-methyl-3-pentanethiol as component B.

(7) The hair dye composition according to (5) above, wherein the stable composition for hair dye further comprises at least one compound selected from isobutyl quinoline, 2,6-nonadienol, 2-methyl-3-methoxypyrazine, amyl cyclopentanone, dihydropentamethyl indanone, 9-decen-1-ol, dihydroanethole, dihydromyrcenol, cis-3-hexenyl acetate, acetyl diisoamylene, 2,6-dimethyl-5-heptenal, acetaldehyde ethyl cis-3-hexenyl acetal, geranyl nitrile, citronellyl nitrile, citronellyl acetate, ethyl benzoate, phenyl ethyl acetate, 3,7-dimethyl-7-methoxyoctan-2-ol, phenyl propyl alcohol, 1-methyl-4-(4-methylpentyl)-3-cyclohexene carbaldehyde, coumarin, 3-pentyl tetrahydropyranyl acetate, and nopyl acetate as component C.

(8) The hair dye composition according to (6) above, wherein the stable composition for hair dye further comprises at least one compound selected from isobutyl quinoline, 2,6-nonadienol, 2-methyl-3-methoxypyrazine, amyl cyclopentanone, dihydropentamethyl indanone, 9-decen-1-ol, dihydroanethole, dihydromyrcenol, cis-3-hexenyl acetate, acetyl diisoamylene, 2,6-dimethyl-5-heptenal, acetaldehyde ethyl cis-3-hexenyl acetal, geranyl nitrile, citronellyl nitrile, citronellyl acetate, ethyl benzoate, phenyl ethyl acetate, 3,7-dimethyl-7-methoxyoctan-2-ol, phenyl propyl alcohol, 1-methyl-4-(4-methylpentyl)-3-cyclohexene carbaldehyde, coumarin, 3-pentyl tetrahydropyranyl acetate, and nopyl acetate as component C.

The stable composition for hair dye according to the present invention has a superior effect in masking the malodor originated from ammonia in the hair color first preparation, is excellent in terms of the stability of odor of the original substance even under a highly alkaline condition (pH 8 to 11), and also has a superior effect in masking the malodor originated from ammonia even after the treatment of hair. In addition, the stable composition for hair dye according to the present invention is excellent in terms of the stability of odor of the original substance even under a strongly acidic condition (pH 2) and also has a superior effect in masking the malodor even after the treatment of hair.

Further, the stable composition for hair dye according to the present invention gives no negative effect on dyeing ability of the hair dye.

DETAILED DESCRIPTION OF THE INVENTION

The following describes the present invention in detail.

In this connection, unless otherwise indicated, all parts, percentages, ratios and the like defined by weight are the same with those by mass, respectively.

As for the specified compounds to be used in the stable composition for hair dye according to the present invention, synthesized ones may be used and a part of compounds may be easily obtained by purchasing commercial products.

That is, as for dihydrocitronellyl nitrile, 2,2,6-trimethylcyclohexane carboxylic acid ethyl ester (Thesaron: trade name of Takasago International Corporation), 2-ethyl-4-(2,2,3-trimethyl-3-cyclopenten-1-yl)-2-buten-1-ol (racemic form and optically active form; preferably, (E)-(R)-form; Levosandol: trade name of Takasago International Corporation), 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, 2-methyl-4-(2,2,3-trimethyl-3-cyclopenten-1-yl)-2-buten-1-ol (racemic form and optically active form; preferably, (E)-(R)-form), tri(cis-3-hexenyl) orthoformate, 4-ethoxy-2-methyl-butanethiol and 5-methoxy-3-methyl-3-pentanethiol, synthesized ones can be used. Further, as for thioglycerin, dibutyl sulfide, thiogeraniol, thiocineol, limonenethiol, 2-methyl-4-propyl-1,3-oxathian, 4-methoxy-2-methyl-2-butanethiol and the like, commercial products may be used. Such fragrances as described above may be racemic compounds or optionally optically active substances in response to uses.

These compounds show excellent effect in masking malodors caused by ammonia and its derivatives formulated particularly in the hair dye first preparation and are also excellent in view of aromatic stability and chemical stability. Also, they are stable in a liquid under an acidic condition and show excellent effect in masking various types of malodors. Further, they do not give a negative effect on the dyeing ability of the hair dye.

Further desirable results can be obtained when a plurality of the compounds defined by the invention are used in combinations. For example, a composition containing, as component A, any one or more compounds selected from dihydrocitronellyl nitrile, 2,2,6-trimethylcyclohexane carboxylic acid ethyl ester, 2-ethyl-4-(2,2,3-trimethyl-3-cyclopenten-1-yl)-2-buten-1-ol, 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, 2-methyl-4-(2,2,3-trimethyl-3-cyclopenten-1-yl)-2-buten-1-ol (racemic form and optically active form; preferably, (E)-(R)-form), and tri(cis-3-hexenyl) orthoformate; and, as component B, any one or more compounds selected from thioglycerin, dibutyl sulfide, thiogeraniol, thiocineol, limonenethiol, 2-methyl-4-propyl-1,3-oxathian, 4-methoxy-2-methyl-2-butanethiol, 4-ethoxy-2-methyl-2-butanethiol, and 5-methoxy-3-methyl-3-pentanethiol shows excellent effect in masking malodors caused by ammonia and its derivatives and is also excellent in view of aromatic stability and chemical stability.

In this regard, dihydrocitronellyl nitrile, 2,2,6-trimethylcyclohexane carboxylic acid ethyl ester, 4,8-dimethyl-7-nonen-2-ol, (E)-(R)-2-methyl-4-(2,2,3-trimethyl-3-cyclopenten-1-yl)-2-buten-1-ol may be the preferable examples as component A, since these compounds are excellent in masking effect, stability of odor and stability of color tone.

Furthermore, thioglycerin, 4-methoxy-2-methyl-2-butanethiol, 4-ethoxy-2-methyl-2-butanethiol, and 5-methoxy-3-methyl-3-pentanethiol may be the preferable examples as component B, since these compounds are excellent in masking effect, stability of odor and stability of color tone.

Component A is contained in the stable composition for hair dye according to the present invention preferably in an amount of 0.1 to 50% by weight, more preferably 1 to 30% by weight, based on the stable composition for hair dye according to the present invention, in order to achieve excellent masking effect, stability of odor and stability of color tone. Further, Component B is contained in the stable composition for hair dye according to the present invention preferably in an amount of 0.01 to 5% by weight, more preferably 0.1 to 3% by weight, based on the stable composition for hair dye according to the present invention, in order to achieve excellent masking effect, stability of odor and stability of color tone.

Though blending ratio of these component A and component B is not particularly limited, it is desirable that the blending ratio of the component A and component B is, for example, component A:component B=99.99:0.01 to 50:50 (by weight ratio) and, more desirably, 99.9:0.1 to 90:10 (by weight ratio).

Component A is available as a compound which is ordinarily used as a fragrance.

On the other hand, component B is a sulfur-containing compound. Ordinarily, many sulfur-containing compounds ordinarily give off a malodor and a mixture blended with any of them comes to give off a malodor. However, among these compounds, component B is a sulfur-containing compound used in fragrance or the like, and when it is used in a small quantity, the malodor is hardly felt, and depending on types, the component may come to give off a pleasant odor.

Although the amount of the component B to be blended varies depending on the type of the compounds to be used in base materials, it can exhibit an effect in a very small amount. Usually, it is preferably from 0.1 ppb to 1% and, more preferably, from 10 ppb to 0.01%, based on the total weight of the hair dye containing the base material. When it goes out of the above-described ranges, a sulfur odor becomes apparent and the stability effect cannot fully be attained.

In the stable composition for hair dye according to the present invention, it is preferable to further add, as component C, any one or more of isobutyl quinoline, 2,6-nonadienol, 2-methyl-3-methoxypyrazine, amyl cyclopentanone, dihydropentamethyl indanone, 9-decen-1-ol, dihydroanethole, dihydromyrcenol, cis-3-hexenyl acetate, acetyl diisoamylene, 2,6-dimethyl-5-heptenal, acetaldehyde ethyl cis-3-hexenyl acetal, geranyl nitrile, citronellyl nitrile, citronellyl acetate, ethyl benzoate, phehyl ethyl acetate, 3,7-dimethyl-7-methoxyoctan-2-ol, phenyl propyl alcohol, 1-methyl-4-(4-methylpentyl)-3-cyclohexene carbaldehyde, 3-pentyl tetrahydropyranyl acetate, and nopyl acetate to the above-described components.

In this regard, isobutyl quinoline, 2,6-nonadienol, dihydroanethole, dihydromyrcenol, cis-3-hexenyl acetate, acetyl diisoamylene and acetaldehyde ethyl cis-3-hexenyl acetal may be the preferable examples as component C, since these compounds are excellent in masking effect, stability of odor and stability of color tone.

Though blending ratios of these component A, component B and component C are not particularly limited, it is desirable that the blending ratios of the component A, component B and component C is, for example, component A+component B:component C=99:1 to 5:95 (by weight ratio) and, more desirably, 95:5 to 20:80 (by weight ratio).

In addition to the components described above, the stable composition for hair dye according to the present invention may still further contain an appropriate component in compliance with the objects, types of the stable composition for hair dye and the like. Examples of the additional components include fragrance components other than those described above, diluents, solvents, and the like.

Examples of the other fragrance components include terpene hydrocarbons such as p-cymene, terpinolene, myrcene and β-caryophylene; aldehydes such as heptanal, octanal, benzaldehyde, salicylic aldehyde, citronellal, α-hexylcinnamic aldehyde and lilial; esters such as methyl jasmonate, methyl dihydrojasmonate, γ-nonyllactone, γ-decalactone and coumarin; ethers such as anisole, p-cresyl methyl ether, β-naphthol methyl ether and β-naphthol ethyl ether; and ketones such as menthone, acetophenone, α-damascone, β-damascone, α-ionone, β-ionone, methyl ionone, irone, dihydrojasmone, cis-jasmone, muscone and civetone. Also included are alcohols such as cis-3-hexenol, heptanol, 2-octanol, benzyl alcohol, citronellol, geraniol, terpineol, tetrahydrogeraniol, anise alcohol, phenylethyl alcohol, phenoxy ethanol, santalol, sandalmysore core, bacdanol, ebanol, polysantol; and natural essential oils such as orange oil, lemon oil, lime oil, patchouli oil, cyprus oil, sandalwood oil, peppermint oil, spearmint oil, and anise oil.

Also, as the diluent and solvent, it is desirable to use dipropylene glycol, ethanol, isopropanol, 3-methoxy-3-propanol and the like from the general purpose point of view.

It is possible to improve masking of various types of malodors originated from the base materials by mixing the stable composition for hair dye according to the present invention to a hair dye composition. That is, it can be used by being optionally mixed to not only the hair dye first preparation which uses large amount of ammonia and alkanolamines as a matter of course, but also with the hair dye first preparation having an oxidizing powder, a pretreatment shampoo for treatment with hair bleach first preparation, hair care products such as shampoo for after-hair dye treatment, hair rinse, hair treatment, hair cream, hair lotion and hair foam. It can also be mixed to the hair dye second preparation, the hair dye second preparation having an oxidizing power or the second preparation of a double preparation type or triple preparation type hair bleach. In this connection, the hair dye composition according to the present invention includes the hair dye first preparation, hair dye second preparation, and hair dye.

In this regard, as the components formulated in the hair dye first preparation to which the stable composition for hair dye according to the present invention is formulated, alkaline chemicals such as ammonia and monoethanolamine; aromatic alcohol-type penetration promoters such as benzylalcohol, phenylethyl alcohol, phenoxyethanol, phenoxyisopropanol, α-methylbenzyl alcohol, α,α-dimethylbenzyl alcohol, α-propylbenzyl alcohol, 2-benzyloxyethanol and 3-benzyloxybutanol, preferably benzylalcohol and 2-benzyloxyethanol; oxidation dye precursors such as p-phenylenediamines, 2,5-diaminopyridines, p-aminophenols, o-aminophenols, o-phenylenediamines, 4,5-aminopyrazols; coupling agents such as methaphenylenediamines, methaaminophenols, methahydroxybenzenes, hydroxyindoles, naphtols and phenols; antioxidizing agents; stabilizing agents and the like may be mentioned. Furthermore, as the components formulated in the hair dye second preparation, chemical oxidizing agents such as hydrogen peroxide, hydrogen peroxide solution (e.g., 35%), urea peroxide, alkali metal bromide, alkali metal per salts (e.g., alkali metal perbromide, alkali metal persulfate and alkali metal perborate), preferably hydrogen peroxide; chelating agents; pH adjusters and the like may be mentioned.

The stable composition for hair dye according to the present invention is blended at an amount of preferably from 0.01 to 30% by weight, particularly preferably from 0.1 to 1.0% by weight based on the total hair dye composition. It is particularly desirable to use the stable composition for hair dye by formulating in a hair treating preparation which contains ammonia, such as the hair dye first preparation having the oxidizing power, because it can mask the malodor originated from ammonia released from the products and the malodor during the use of hair dyes and after the hair treatment.

The stable composition for hair dye according to the present invention shows superior effect in masking the malodor originated from ammonia when mixed to the hair dye first preparation, also shows excellent aromatic stability under a relatively high temperature condition of 45° C. for a prolonged period of 3 months, and further shows superior effect in masking the malodor originated from ammonia and other malodors even after the treatment of hair with the hair dye first preparation and hair dye second preparation.

EXAMPLES

The following describes the present invention further in detail with reference to Examples, but the present invention is not restricted by these Examples.

Example 1

A hair dye first preparation was prepared based on the formulation as described below. In this connection, illustrative examples of the stable composition for hair dye in the formulation are shown in Tables 1 to 3.

| Component | % by weight |
|---|---|
| Toluene-2,5-diamine aqueous solution (20%) | 7.0 |
| p-Aminophenol | 2.0 |
| m-Hydroxybenzene | 0.4 |
| Anhydrous sodium sulfite | 0.4 |
| Disodium edetate | 0.3 |
| Aqueous ammonia (28%) | 7.0 |
| Ammonium chloride | 3.5 |
| Ethanol (95%) | 15.0 |
| Lauric acid | 5.0 |
| Diethanolamide laurate | 14.5 |
| Polyoxyethylene (20) octyldodecyl ether | 10.0 |
| Propylene glycol | 10.0 |
| Stable composition for hair dye | 0.2 |
| Purified water | balance |
| Total | 100.0 |

(Evaluation)

Effect of the hair dye first preparation to mask the malodor originated from the ammoniacal malodor, stability of its odor and stability of color tone were evaluated by the evaluation method as described below.

(Evaluation Method)

(1) Masking Effect on the Malodor Originated from the Ammoniacal Malodor

The hair dye first preparation was stored at 37° C. for 12 weeks, and then, a malodor-masking effect thereof was evaluated by a sensory test based on the following criteria:
1: very good; 2: good; 3: usual; 4: bad; and 5: very bad.

(2) Stability Effect of Odor

A hair dye treatment was carried out by a conventional method using the hair dye first preparation. Changing degree of the aromatic tone at the bottle mouth when the container was opened before the treatment was evaluated by a sensory test based on the following criteria:
1: not changed; 2: not much changed; 3: slightly changed; 4: fairly changed; and 5: greatly changed.

(3) Stability Effect of Color Tone

The hair dye first preparation was stored at 37° C. for 12 weeks, and then, the stability effect of color tone of the hair dye was evaluated by a sensory test based on the following criteria:
1: very good; 2: good; 3: usual; 4: bad; and 5: very bad.

Results of the evaluations by the evaluation methods are shown in Tables 1 to 3. In this connection, the "masking effect" in the table is an evaluation result by the above evaluation method (1), the "stability of odor" is an evaluation result by the above evaluation method (2), and the "stability effect or color tone" is an evaluation result by the above evaluation method (3).

TABLE 1

| Stable composition for hair dye (fragrance 100%) | Masking effect | Stability of odor | Stability of color tone |
| --- | --- | --- | --- |
| Dihydrocitronellyl nitrile | 2.0 | 1.7 | 1.3 |
| 2,2,6-Trimethylcyclohexane carboxylic acid ethyl ester | 2.0 | 2.0 | 1.0 |
| (E)-(R)-2-Ethyl-4-(2,2,3-trimethyl-3-cyclopenten-1-yl)-2-buten-1-ol | 3.0 | 3.3 | 1.0 |
| 2,2,6-Trimethylcyclohexyl-3-hexanol | 3.3 | 3.3 | 2.7 |
| Cyclohexadecenone | 2.0 | 2.3 | 1.0 |
| 1-(2-Methyl-2-propenyloxy)-2,2,4-trimethylpentan-3-ol | 2.7 | 2.7 | 1.3 |
| 1-Phenyl-2,2,4-trimethyl-3-pentanone | 2.7 | 3.0 | 2.3 |
| 4,8-Dimethyl-7-nonen-2-ol | 2.0 | 2.0 | 1.0 |
| (E)-(R)-2-Methyl-4-(2,2,3-trimethyl-3-cyclopenten-1-yl)-2-buten-1-ol | 2.0 | 2.0 | 1.0 |
| Tri(cis-3-hexenyl) orthoformate | 3.0 | 3.0 | 1.0 |

TABLE 2

| Stable composition for hair dye (fragrance 100%) | Masking effect | Stability of odor | Stability of color tone |
| --- | --- | --- | --- |
| Thioglycerin | 2.0 | 2.0 | 1.0 |
| Dibutyl sulfide | 2.3 | 2.0 | 1.0 |
| Thiogeraniol | 2.3 | 2.0 | 1.0 |
| Thiocineol | 2.3 | 3.0 | 1.0 |
| Limonenethiol | 2.3 | 2.0 | 1.0 |
| 2-Methyl-4-propyl-1,3-oxathian | 2.0 | 2.3 | 1.0 |
| 4-Methoxy-2-methyl-2-butanethiol | 1.7 | 2.0 | 1.0 |
| 4-Ethoxy-2-methyl-2-butanethiol | 2.0 | 2.0 | 1.0 |

TABLE 2-continued

| Stable composition for hair dye (fragrance 100%) | Masking effect | Stability of odor | Stability of color tone |
| --- | --- | --- | --- |
| 5-Methoxy-3-methyl-3-pentanethiol | 2.0 | 2.0 | 1.0 |

TABLE 3

| Stable composition for hair dye (fragrance 100%) | Masking effect | Stability of odor | Stability of color tone |
| --- | --- | --- | --- |
| Isobutyl quinoline | 1.7 | 1.0 | 2.0 |
| 2,6-Nonadienol | 1.3 | 1.3 | 1.3 |
| 2-Methyl-3-methoxypyrazine | 1.7 | 1.3 | 4.0 |
| Amyl cyclopentanone | 2.3 | 1.7 | 4.7 |
| Dihydropentamethyl indanone | 2.0 | 2.0 | 2.3 |
| 9-Decen-1-ol | 2.0 | 2.0 | 3.0 |
| Dihydroanethole | 2.0 | 2.0 | 1.3 |
| Dihydromyrcenol | 2.0 | 2.0 | 1.0 |
| Cis-3-hexenyl acetate | 2.0 | 2.0 | 1.3 |
| Acetyl diisoamylene | 2.0 | 2.0 | 1.7 |
| 2,6-Dimethyl-5-heptenal | 2.0 | 2.0 | 3.0 |
| Acetaldehyde ethyl cis-3-hexenyl acetal | 2.0 | 2.0 | 1.0 |
| Geranyl nitrile | 2.3 | 2.0 | 2.3 |
| Citronellyl nitrile | 2.7 | 2.0 | 1.0 |
| Citronellyl acetate | 3.3 | 3.3 | 1.3 |
| Ethyl benzoate | 3.3 | 3.3 | 2.3 |
| Phenyl ethyl acetate | 3.3 | 3.3 | 2.3 |
| 3,7-Dimethyl-7-methoxyoctan-2-ol | 3.0 | 3.3 | 2.7 |
| Phenyl propyl alcohol | 2.7 | 3.3 | 1.3 |
| 1-Methyl-4-(4-methylpentyl)-3-cyclohexene carbaldehyde | 2.7 | 3.3 | 1.3 |
| Coumarin | 3.3 | 3.3 | 2.3 |
| 3-Pentyl tetrahydropyranyl acetate | 3.3 | 3.3 | 2.0 |
| Nopyl acetate | 2.7 | 3.3 | 1.3 |

As is evident from the results shown in Tables 1 to 3, it was revealed that all preparations of the present invention have high masking effect and are excellent in terms of stability of odor and stability of color tone.

Example 2

A hair dye first preparation containing the stable composition for hair dye as shown below and based on the formulation described in Example 1 was obtained.

| Stable composition for hair dye (Fragrance compound) | |
| --- | --- |
| Component | % by weight |
| Cyclohexadecenone | 5.0 |
| Cashmerane | 2.0 |
| 4,8-Dimethyl-7-nonen-2-ol | 10.0 |
| (E)-(R)-2-Methyl-4-(2,2,3-trimethyl-3-cyclopenten-1-yl)-2-buten-1-ol | 3.0 |
| Tri(cis-3-hexenyl) orthoformate | 5.0 |
| 1-Phenyl-2,2,4-trimethyl-3-pentanone | 5.0 |
| Dihydrocitronellyl nitrile | 5.0 |
| 5-Methoxy-3-methyl-3-pentanethiol (10% dipropylene glycol solution) | 1.0 |
| 4-Ethoxy-2-methyl-2-butanethiol (10% dipropylene glycol solution) | 1.0 |
| Delphone | 1.0 |
| 1-(2-Methyl-2-propenyloxy)-2,2,4-trimethylpentan-3-ol | 10.0 |
| 2,2,6-trimethylcyclohexane carboxylic acid ethyl ester | 10.0 |

-continued

Stable composition for hair dye (Fragrance compound)

| Component | % by weight |
|---|---|
| (E)-(R)-2-Ethyl-4-(2,2,3-trimethyl-3-cyclopenten-1-yl)-2-buten-1-ol | 7.0 |
| Phenyl ethyl alcohol | 5.0 |
| Muguet base | 10.0 |
| Rose base | 15.0 |
| Musk base | 5.0 |
| Total | 100.0 |

(Evaluation)

Effect of the above hair dye first preparation to mask the malodor originated from the ammoniacal malodor, stability of its odor and stability of color tone were evaluated in the same manner as in Example 1. That is, (1) masking effect on the malodor originated from the ammoniacal malodor, (2) stability effect of odor when a hair treatment was carried out by a conventional method using the hair dye first preparation and (3) stability effect of color tone of the hair dye first preparation was evaluated in the same manner as in Example 1. The results are shown in Table 4.

TABLE 4

|  | Masking effect | Stability of odor | Stability of color tone |
|---|---|---|---|
| Stable composition for hair dye (Fragrance compound) | 1.3 | 1.3 | 1.0 |

As is evident from the results shown in Table 4, the stable composition for hair dye containing the compounds according to the present invention is excellent in stability and has a high masking effect.

Example 3

A hair dye second preparation was prepared in accordance with the formulation as shown below. In this connection, as the illustrative example of the stable composition for hair dye in the formulation, the stable composition for hair dye as used in Example 2 was used.

| Component | % by weight |
|---|---|
| Phenacetin | 0.1 |
| Diphenyl ether | 0.2 |
| Ethanol (95%) | 2.0 |
| Citric acid | proper amount |
| Hydrogen peroxide (35%) | 17.0 |
| Propylene glycol | 5.0 |
| Stable composition for hair dye | 0.2 |
| Purified water | balance |
| Total | 100.0 |

(Evaluation)

Masking effect of the hair dye second preparation, stability of its odor and stability of color tone were evaluated by the evaluation method described below.

(Evaluation Method)

(4) Masking Effect

The hair dye second preparation was stored at 37° C. for 12 weeks, and then, a masking effect thereof was evaluated by a sensory test based on the following criteria:
1: very good; 2: good; 3: usual; 4: bad; and 5: very bad.

(5) Stability of Odor

A hair dye treatment was carried out by a conventional method using the hair dye second preparation. Changing degree of the aromatic tone at a bottle mouth when a container was opened before the treatment was evaluated by a sensory test based on the following criteria:
1: not changed; 2: not much changed; 3: slightly changed; 4: fairly changed; and 5: greatly changed.

(6) Stability of Color Tone

The hair dye second preparation was stored at 37° C. for 12 weeks, and then, a stability effect of color tone thereof was evaluated by a sensory test based on the following criteria:
1: very good; 2: good; 3: usual; 4: bad; and 5: very bad.

Results of the evaluations by the evaluation methods are shown in Table 5. In this connection, the "masking effect" in the table is an evaluation result by the evaluation method (4), the "stability of odor" is an evaluation result by the evaluation method (5), and the "stability effect of a color tone" is an evaluation result by the evaluation method (6).

TABLE 5

|  | Masking effect | Stability of odor | Stability of color tone |
|---|---|---|---|
| Stable composition for hair dye (Fragrance compound) | 2.0 | 1.3 | 1.0 |

As shown in Table 5, the odor and color tone are highly stable even in the hair dye second preparation (acidic, pH=2), and the stable composition for hair dye according to the present invention not only masks the ammoniacal malodor but also shows high stability even after subsequent hair dye treatment by a conventional method, showing no change of quality in odor.

While the invention has been described in detail and with reference to specific embodiments thereof, it will be apparent to one skilled in the art that various changes and modifications can be made therein without departing from the scope thereof.

This application is based on Japanese patent application No. 2005-107223 filed Apr. 4, 2005, the entire contents thereof being hereby incorporated by reference.

What is claimed is:

1. A method for stabilizing odor or color of a hair dye composition, which comprises incorporating into the hair dye composition at least one compound selected from dihydrocitronellyl nitrile, 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, tri(cis-3-hexenyl) orthoformate, thioglycerin, dibutyl sulfide, thiogeraniol, thiocineol, limonenethiol, 2-methyl-4-propyl-1,3-oxathian, 4-methoxy-2-methyl-2-butanethiol, 4-ethoxy-2-methyl-2-butanethiol, and 5-methoxy-3-methyl-3-pentanethiol.

2. A method for stabilizing odor or color of a hair dye composition, which comprises:
incorporating into the hair dye composition at least one compound selected from the group consisting of dihydrocitronellyl nitrile, 2,2,6-trimethylcyclohexane carboxylic acid ethyl ester, 2-ethyl-4-(2,2,3-trimethyl-3- cyclopenten-1-yl)-2-buten-1-ol, 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, 2-methyl-4-(2,2,3-trimethyl-3-cyclopenten-1-yl)-2-buten-1-ol, and tri(cis-3-hexenyl) orthoformate; and at least one compound selected from the group consisting of thioglycerin, dibutyl sulfide, thiogeraniol, thiocineol, limonenethiol, 2-methyl-4-propyl-1,3-oxathian, 4-methoxy-2-methyl-2-butanethiol, 4-ethoxy-2-methyl-2-butanethiol, and 5-methoxy-3-methyl-3-pentanethiol.

3. The method according to claim 1, which further comprises incorporating into the hair dye composition at least one compound selected from the group consisting of isobutyl quinoline, 2,6-nonadienol, 2-methyl-3-methoxypyrazine, amyl cyclopentanone, dihydropentamethyl indanone, 9-decen-1-ol, dihydroanethole, dihydromyrcenol, cis-3-hexenyl acetate, acetyl diisoamylene, 2,6-dimethyl-5-heptenal, acetaldehyde ethyl cis-3-hexenyl acetal, geranyl nitrile, citronellyl nitrile, citronellyl acetate, ethyl benzoate, phenyl ethyl acetate, 3,7-dimethyl-7-methoxyoctan-2-ol, phenyl propyl alcohol, 1-methyl-4-(4-methylpentyl)-3-cyclohexene carbaldehyde, coumarin, 3-pentyl tetrahydropyranyl acetate, and nopyl acetate.

4. The method according to claim 2, which further comprises incorporating into the hair dye composition at least one compound selected from the group consisting of isobutyl quinoline, 2,6-nonadienol, 2-methyl-3-methoxypyrazine, amyl cyclopentanone, dihydropentamethyl indanone, 9-decen-1-ol, dihydroanethole, dihydromyrcenol, cis-3-hexenyl acetate, acetyl diisoamylene, 2,6-dimethyl-5-heptenal, acetaldehyde ethyl cis-3-hexenyl acetal, geranyl nitrile, citronellyl nitrile, citronellyl acetate, ethyl benzoate, phenyl ethyl acetate, 3,7-dimethyl-7-methoxyoctan-2-ol, phenyl propyl alcohol, 1-methyl-4-(4-methylpentyl)-3-cyclohexene carbaldehyde, coumarin, 3-pentyl tetrahydropyranyl acetate, and nopyl acetate.

5. A stable hair dye composition, comprising:
at least one compound selected from the group consisting of dihydrocitronellyl nitrile, 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, tri(cis-3-hexenyl) orthoformate, thioglycerin, dibutyl sulfide, thiogeraniol, thiocineol, limonenethiol, 2-methyl-4-propyl-1,3-oxathian, 4-methoxy-2-methyl-2-butanethiol, 4-ethoxy-2-methyl-2-butanethiol, and 5-methoxy-3-methyl-3-pentanethiol.

6. A stable hair dye composition, comprising:
at least one compound selected from the group consisting of dihydrocitronellyl nitrile, 2,2,6-trimethylcyclohexane carboxylic acid ethyl ester, 2-ethyl-4-(2,2,3-trimethyl-3-cyclopenten-1-yl)-2-buten-1-ol, 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, 2-methyl-4-(2,2,3-trimethyl-3-cyclopenten-1-yl)-2-buten-1-ol, and tri(cis-3-hexenyl) orthoformate; and at least one compound selected from the group consisting of thioglycerin, dibutyl sulfide, thiogeraniol, thiocineol, limonenethiol, 2-methyl-4-propyl-1,3-oxathian, 4-methoxy-2-methyl-2-butanethiol, 4-ethoxy-2-methyl-2-butanethiol, and 5-methoxy-3-methyl-3-pentanethiol.

7. A stable hair dye composition, comprising:
at least one compound selected from the group consisting of dihydrocitronellyl nitrile, 2,2,6-trimethylcyclohexane carboxylic acid ethyl ester, 2-ethyl-4-(2,2,3-trimethyl-3-cyclopenten-1-yl)-2-buten-1-ol, 2,2,6-trimethylcyclohexyl-3-hexanol, cyclohexadecenone, 1-(2-methyl-2-propenyloxy)-2,2,4-trimethylpentan-3-ol, 1-phenyl-2,2,4-trimethyl-3-pentanone, 4,8-dimethyl-7-nonen-2-ol, 2-methyl-4-(2,2,3-trimethyl-3-cyclopenten-1-yl)-2-buten-1-ol, tri(cis-3-hexenyl) orthoformate, thioglycerin, dibutyl sulfide, thiogeraniol, thiocineol, limonenethiol, 2-methyl-4-propyl-1,3-oxathian, 4-methoxy-2-methyl-2-butanethiol, 4-ethoxy-2-methyl-2-butanethiol, and 5-methoxy-3-methyl-3-pentanethiol; and at least one compound selected from the group consisting of isobutyl quinoline, 2,6-nonadienol, 2-methyl-3-methoxypyrazine, amyl cyclopentanone, dihydropentamethyl indanone, 9-decen-1-ol, dihydroanethole, dihydromyrcenol, cis-3-hexenyl acetate, acetyl diisoamylene, 2,6-dimethyl-5-heptenal, acetaldehyde ethyl cis-3-hexenyl acetal, geranyl nitrile, citronellyl nitrile, citronellyl acetate, ethyl benzoate, phenyl ethyl acetate, 3,7-dimethyl-7-methoxyoctan-2-ol, phenyl propyl alcohol, 1-methyl-4-(4-methylpentyl)-3-cyclohexene carbaldehyde, coumarin, 3-pentyl tetrahydropyranyl acetate, and nopyl acetate.

8. The stable hair dye composition according to claim 6, comprising at least one compound selected from the group consisting of isobutyl quinoline, 2,6-nonadienol, 2-methyl-3-methoxypyrazine, amyl cyclopentanone, dihydropentamethyl indanone, 9-decen-1-ol, dihydroanethole, dihydromyrcenol, cis-3-hexenyl acetate, acetyl diisoamylene, 2,6-dimethyl-5-heptenal, acetaldehyde ethyl cis-3-hexenyl acetal, geranyl nitrile, citronellyl nitrile, citronellyl acetate, ethyl benzoate, phenyl ethyl acetate, 3,7-dimethyl-7-methoxyoctan-2-ol, phenyl propyl alcohol, 1-methyl-4-(4-methylpentyl)-3-cyclohexene carbaldehyde, coumarin, 3-pentyl tetrahydropyranyl acetate, and nopyl acetate.

* * * * *

UNITED STATES PATENT AND TRADEMARK OFFICE
CERTIFICATE OF CORRECTION

| | | |
|---|---|---|
| PATENT NO. | : 7,399,318 B2 | |
| APPLICATION NO. | : 11/384306 | |
| DATED | : July 15, 2008 | |
| INVENTOR(S) | : Junko Nagano et al. | |

It is certified that error appears in the above-identified patent and that said Letters Patent is hereby corrected as shown below:

ON THE TITLE PAGE [56] REFERENCES CITED:

FOREIGN PATENT DOCUMENTS, "JP   2003-344638   12/2000" should read --JP   2000-344638   12/2000--.

COLUMN 1:

Line 36, "has" should read --have--.

COLUMN 2:

Line 51, "The-present" should read --The present--.

COLUMN 3:

Line 16, "followings." should read --following.--; and
    Line 34, "composition" should read --composition:--.

COLUMN 4:

Line 23, "comprising" should read --comprising:--.

COLUMN 6:

Line 30, "is," should read --be,--; and
    Line 39, "comes to give" should read --ends up giving--.

UNITED STATES PATENT AND TRADEMARK OFFICE
CERTIFICATE OF CORRECTION

PATENT NO. : 7,399,318 B2
APPLICATION NO. : 11/384306
DATED : July 15, 2008
INVENTOR(S) : Junko Nagano et al.

It is certified that error appears in the above-identified patent and that said Letters Patent is hereby corrected as shown below:

<u>COLUMN 7</u>:

Line 7, "is," should read --be,--.

<u>COLUMN 14</u>:

Line 42, "comprising" should read --further comprising--.

Signed and Sealed this

Fourth Day of November, 2008

JON W. DUDAS
*Director of the United States Patent and Trademark Office*